United States Patent
Linder et al.

(10) Patent No.: US 6,317,628 B1
(45) Date of Patent: Nov. 13, 2001

(54) CARDIAC RHYTHM MANAGEMENT SYSTEM WITH PAINLESS DEFRIBILLATION LEAD IMPEDANCE MEASUREMENT

(75) Inventors: William J. Linder, Golden Valley; Keith R. Maile, New Brighten, both of MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 09/236,911

(22) Filed: Jan. 25, 1999

(51) Int. Cl.[7] .......................................... A61N 1/39
(52) U.S. Cl. .................. 600/547; 607/8; 607/6; 607/63
(58) Field of Search ................... 607/5, 6, 7, 8, 607/28, 63; 600/547

(56) References Cited

U.S. PATENT DOCUMENTS

| | | | |
|---|---|---|---|
| 4,870,341 | 9/1989 | Pihl et al. | 324/57 R |
| 4,880,004 | 11/1989 | Baker, Jr. et al. | 128/419 |
| 5,076,272 | 12/1991 | Ferek-Petric | 128/419 |
| 5,088,489 | 2/1992 | Lerman | 128/419 |
| 5,179,946 * | 1/1993 | Weiss | 607/4 |
| 5,231,987 | 8/1993 | Robson | 607/29 |
| 5,487,754 | 1/1996 | Snell et al. | 607/27 |
| 5,487,755 | 1/1996 | Snell et al. | 607/27 |
| 5,654,030 | 8/1997 | Munshi et al. | 427/2.24 |
| 5,683,443 | 11/1997 | Munshi et al. | 607/121 |
| 5,713,935 | 2/1998 | Prutchi et al. | 607/28 |
| 5,722,997 | 3/1998 | Nedungadi et al. | 607/28 |
| 5,814,088 | 9/1998 | Paul et al. | 607/28 |
| 6,022,322 * | 2/2000 | Prutchi | 600/506 |
| 6,076,015 * | 6/2000 | Hartley et al. | 607/20 |
| 6,104,949 * | 8/2000 | Crick et al. | 600/547 |
| 6,104,954 * | 8/2000 | Blunsden | 607/8 |

FOREIGN PATENT DOCUMENTS

| | | | |
|---|---|---|---|
| 0588124 | 3/1994 | (EP) | A61N/1/39 |
| 98/47563 | 10/1998 | (WO) | A61N/1/39 |

\* cited by examiner

*Primary Examiner*—Kennedy Schaetzle
(74) *Attorney, Agent, or Firm*—Schwegman, Lundberg, Woessner & Kluth, P.A.

(57) ABSTRACT

A cardiac rhythm management system includes a defibrillation lead impedance measurement system by which defibrillation lead impedance is measured using a test current source different from the defibrillation output supply. A resulting voltage is measured to determine the defibrillation lead impedance. Using low amplitude test currents (e.g., 10–20 milliamperes) avoids patient discomfort. Charge-balanced test currents avoids charge build-up that may interfere with sensing and avoids electrode degeneration. Different current amplitudes and resulting measured voltages provide a differential defibrillation lead impedance measurement for canceling undesired effects. Bidirectional test currents account for polarity effects on the defibrillation lead impedance measurement. A calibration/correction technique uses measurements of known resistances to correct a measurement of an unknown defibrillation lead impedance measurement.

28 Claims, 12 Drawing Sheets

CARDIAC RHYTHM MANAGEMENT SYSTEM WITH PAINLESS DEFRIBILLATION LEAD IMPEDANCE MEASUREMENT

FIELD OF THE INVENTION

This invention relates generally to cardiac rhythm management systems and particularly, but not by way of limitation, to a cardiac rhythm management system with a painless shocking lead impedance measurement circuit.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias is via drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, or pacers. Pacers deliver timed sequences of low energy electrical stimuli, called pace pulses, to the heart, such as via a transvenous leadwire having one or more electrodes disposed in the heart. Heart contractions are initiated in response to such pace pulses. By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other systems or devices for diagnosing or treating cardiac arrhythmias.

One problem that arises in cardiac rhythm management devices is in determining defibrillation or "shocking" lead impedance. The defibrillation lead impedance includes the effective resistance of the leadwire that couples the cardiac rhythm management device to the heart for delivering the electrical defibrillation countershock at defibrillation electrodes located at or near the heart. The defibrillation lead impedance also includes the effective resistance of the body tissue (e.g., the heart) and body fluids located between the defibrillation electrodes. The defibrillation lead impedance due to the leadwire and heart resistance is generally around 50 Ω, but can range from 15 Ω to 100 Ω.

The value of the defibrillation lead impedance provides useful information. For example, an extremely low lead impedance value may indicate a short circuit between the defibrillation electrodes. An extremely large lead impedance value may indicate an open circuit such as, for example, resulting from a leadwire that has become disconnected from the cardiac rhythm management device. Both defective leadwire conditions must be detected and remedied if the cardiac rhythm management device is to provide effective defibrillation countershock therapy to the heart.

It is possible to calculate defibrillation lead impedance, for example, by delivering an electrical defibrillation countershock to the heart. By measuring a voltage droop of the defibrillation countershock voltage pulse, the effective resistance of the defibrillation lead can be estimated. However, delivering a defibrillation countershock is painful to the patient. As a result, such techniques cannot be performed routinely, periodically, or even occasionally, because measuring defibrillation lead impedance because significant patient discomfort would likely result. Moreover, measuring defibrillation lead impedance is particularly difficult because of the high voltages (e.g., 750 Volts) being delivered to the heart during the defibrillation countershock. Typical measurement integrated circuits are not capable of withstanding such high voltages. In summary, there exists a need for a technique of measuring defibrillation lead impedance without inflicting pain on the patient from delivering a defibrillation countershock to measure defibrillation lead impedance.

SUMMARY

The present cardiac rhythm management system provides, among other things, a defibrillation lead impedance measurement system. Instead of measuring defibrillation lead impedance by delivering a high energy or low energy defibrillation countershock and measuring a resulting voltage, defibrillation lead impedance is measured using a test current source that is different from the defibrillation output supply. A voltage resulting from the test current flowing through the defibrillation lead and heart resistance is measured. The defibrillation lead impedance is determined from the measured voltage.

Because low amplitude test current pulses are used (e.g., 10–20 milliamperes), the defibrillation lead impedance measurement would not cause significant pain or discomfort to the patient. As a result, the defibrillation lead impedance can be measured routinely for diagnostic or other purposes.

In one embodiment, the test currents are charge-balanced, i.e., a first test current pulse waveform sourced at a particular defibrillation electrode is offset by a substantially equal amount of charge sunk at that defibrillation electrode by a second test current pulse waveform, because the first and second test currents flow in opposite directions. This avoids charge build-up in the heart that may increase the difficulty of sensing intrinsic electrical heart activity signals. It also avoids degeneration of the defibrillation electrodes by electroplating or corrosion.

One embodiment provides test current pulses of at least two different steady-state amplitude steps. Defibrillation lead impedance is determined differentially by measuring a voltage associated with each test current amplitude step, and dividing a difference of the measured voltage by a corresponding difference in the test current amplitudes. This technique allows cancellation of a component of the measured voltage that is not associated with the desired defibrillation lead impedance measurement.

Another embodiment provides bidirectional test currents to account for polarity effects on the defibrillation lead impedance measurement. A further embodiment provides a calibration/correction technique in which measurements of known resistances are used to correct a measurement of an unknown defibrillation lead impedance measurement. Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views.

DETAILED DESCRIPTION

Figure 1:
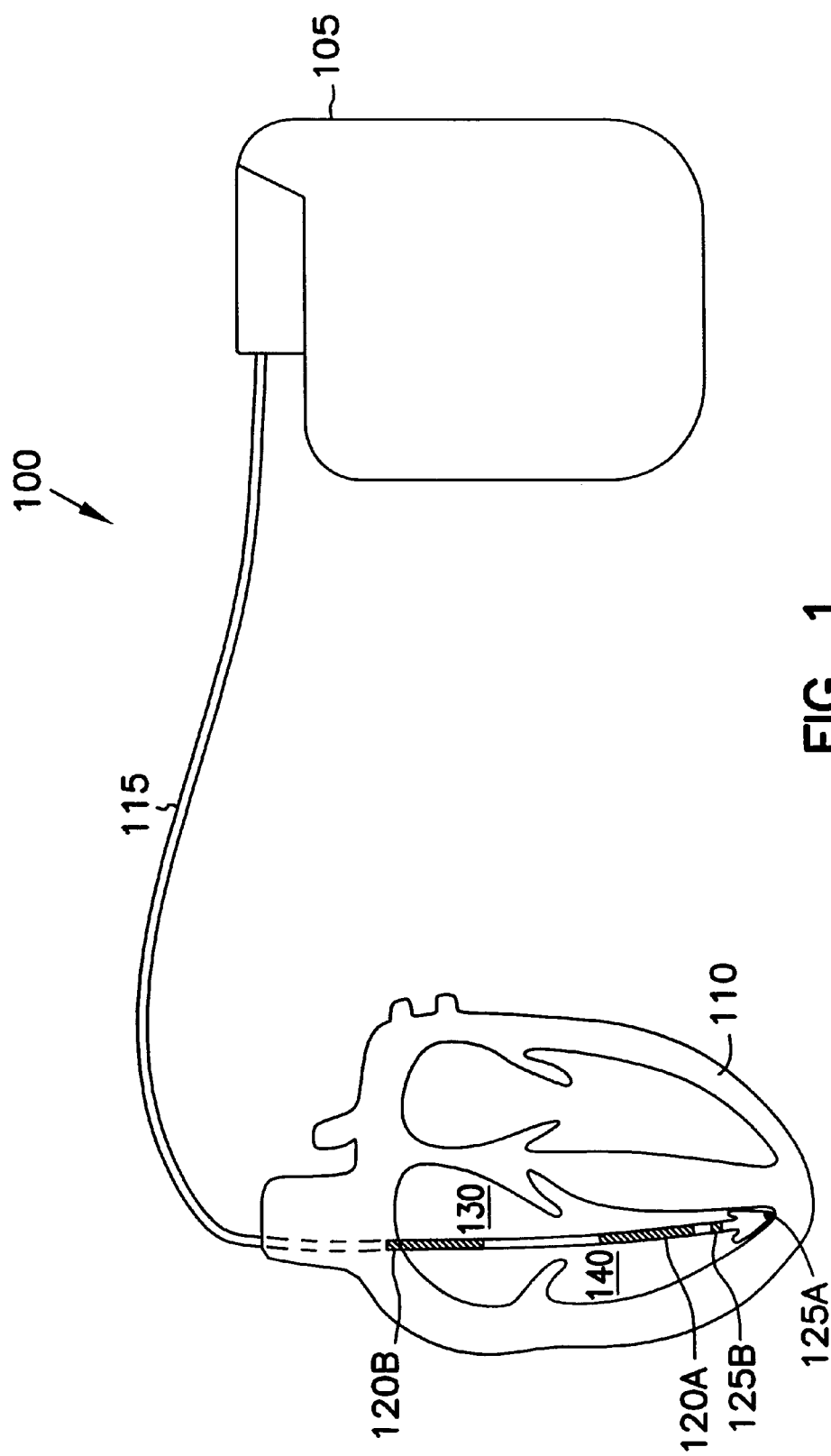
FIG. 1 is a generalized schematic diagram illustrating one embodiment of a portion of a cardiac rhythm management system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views.

SYSTEM OVERVIEW

The present system provides, among other things, a cardiac rhythm management system that provides a painless technique of measuring defibrillation lead impedances without delivering a painful high voltage defibrillation countershock. As a result, the defibrillation lead impedance measurement can be performed occasionally, periodically, or even routinely because performing the measurement does not cause discomfort to the patient. Moreover, the present technique allows a defibrillation countershock therapy to be dynamically adjusted, based at least partially on the measured values of defibrillation lead impedance. Furthermore, the present system uses test stimuli energies (e.g., amplitude and pulsewidth) that are less than the energy required to "capture" the heart (i.e., less than the "pacing threshold" energy that causes a resulting depolarization and heart contraction), ensuring that the present system is both painless and nondisruptive to the underlying paced or intrinsic heart rhythm.

In this document, defibrillation lead impedance is understood to refer to resistance, and not to associated reactive components. Also, defibrillation lead impedance is understood to refer only to a lead impedance that is associated with electrodes that deliver a defibrillation countershock to the heart, and not to the lead impedance associated with pacing electrodes that deliver only pacing pulses to the heart.

FIG. 1 is a generalized schematic diagram illustrating generally, by way of example, but not by way of limitation, one embodiment of a portion of a cardiac rhythm management system 100. Various embodiments of system 100 include external or implantable pacer/defibrillators, cardioverters, defibrillators, any combination of the foregoing, or any other system using or maintaining cardiac rhythms.

In the embodiment of FIG. 1, cardiac rhythm management system 100 includes a cardiac rhythm management device 105 coupled to heart 110 via one or more endocardial or epicardial leadwires, such a pacing leadwire or a defibrillation leadwire 115. Defibrillation leadwire 115 includes one or more defibrillation electrodes, such as for delivering defibrillation countershock ("shock") therapy via first defibrillation electrode 120A and/or second defibrillation electrode 120B. Defibrillation leadwire 115 may also include additional electrodes, such as for delivering pacing therapy via first pacing electrode 125A (e.g., a "tip" electrode) and/or second pacing electrode 125B (e.g., a "ring" electrode). Defibrillation electrodes 120A–B and pacing electrodes 125A–B are typically disposed in or near one or more chambers of heart 110.

In the embodiment of FIG. 1, defibrillation leadwire 115 includes multiple conductors that are insulated from each other for providing independent connections between each electrode and cardiac rhythm management device 105. In one embodiment, the defibrillation leadwire is secured to heart 110, such as by a corkscrew, a barb, or similar mechanism at or near first pacing electrode 125A. In another embodiment, cardiac rhythm management device 105 includes a hermetically sealed casing, a portion of which provides a conductive electrode that operates in conjunction with at least one of the electrodes disposed in heart 110 for delivering pacing pulses and/or defibrillation countershocks and/or sensing electrical heart activity signals.

Defibrillation Lead Impedance Measurement Hardware Example 1

Figure 2:
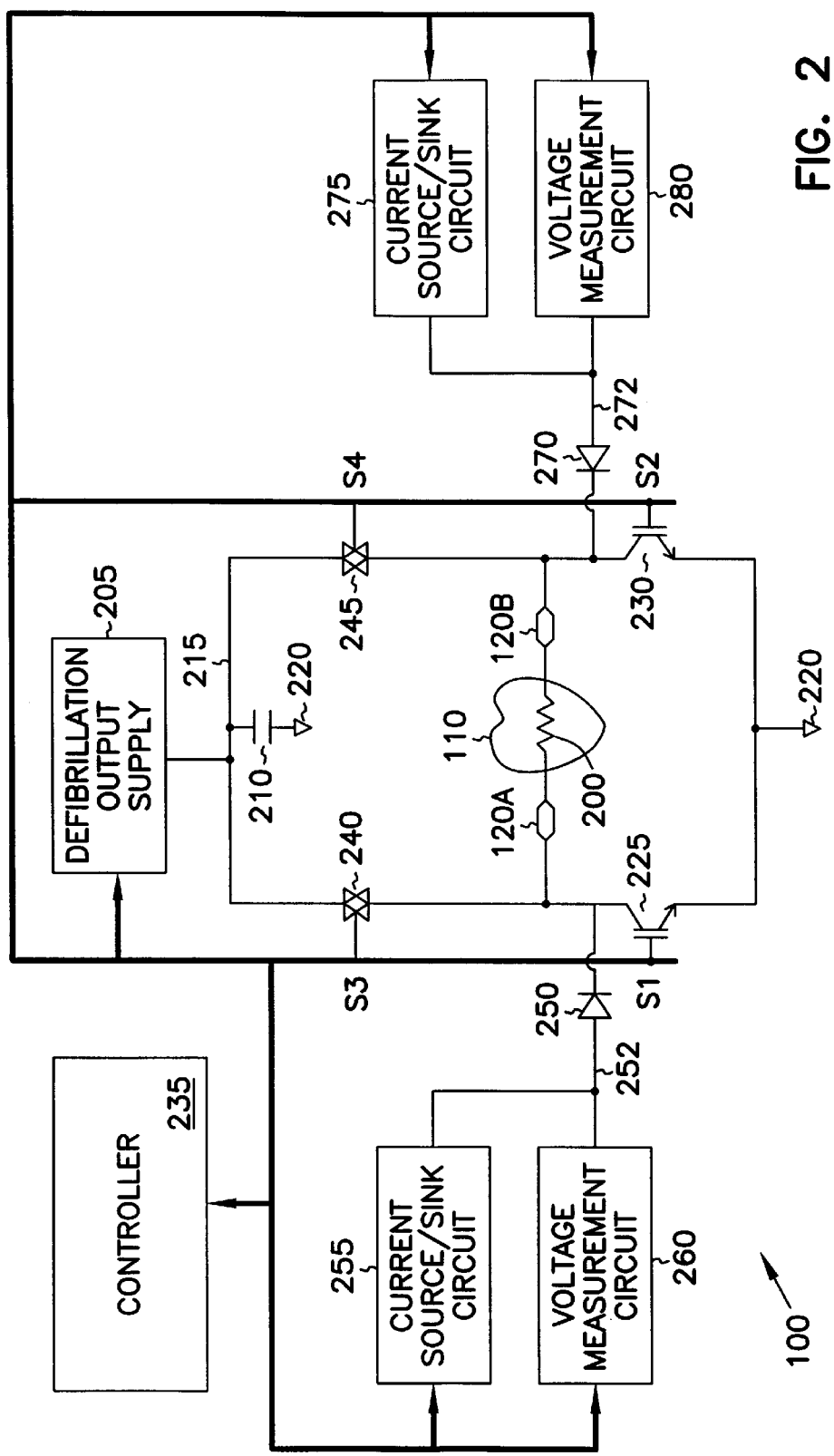
FIG. 2 is a generalized schematic/block diagram illustrating a first example of portions of the cardiac rhythm management system for measuring defibrillation lead impedance.

FIG. 2 is a generalized schematic/block diagram illustrating generally, by way of example, but not by way of limitation one embodiment of portions of system 100. First defibrillation electrode 120A and second defibrillation electrode 120B are illustrated as being coupled to heart 110. Heart resistance 200 is interposed between first and second defibrillation electrodes 120A–B. System 100 includes a defibrillation output supply 205 which generates a defibrillation countershock energy. The defibrillation countershock energy is stored as a high positive voltage (e.g., approximately between 700 Volts and 750 Volts) on a storage capacitor 210 that is coupled between high voltage node 215 and ground node 220.

First switch 225 and second switch 230 are, in one example, insulated gate bipolar transistors (IGBTs) or other switching devices that couple the respective first and second defibrillation electrodes 120A–B to ground node 220. In one embodiment, first switch 225 includes a collector coupled to first defibrillation electrode 120A, a gate coupled to receive a control signal S1, such as from controller 235, and an emitter coupled to ground node 220. Second switch 230 includes a collector coupled to second defibrillation electrode 120B, a gate coupled to receive a control signal S2, such as from controller 235, and an emitter coupled to ground node 220.

Third switch 240 and fourth switch 245 are, in one example, triacs, thyristors, semiconductor-controlled rectifiers (SCRs), four-layer diodes or other switching devices that couple high voltage node 215 to first and second defibrillation electrodes 120A–B, respectively. In one embodiment, control signals S3 and S4 are received from controller 235 to control operation of third switch 240 and fourth switch 245, respectively.

First diode 250 includes a cathode coupled to first defibrillation electrode 120A and an anode coupled at node 252 to lead impedance stimulation and measurement circuits, such as first current source and/or sink circuit 255 and first voltage measurement circuit 260. Second diode 270 includes a cathode coupled to second defibrillation electrode 120B and an anode coupled at node 272 to lead impedance stimulation and measurement circuits, such as second current source and/or sink circuit 275 and second voltage measurement circuit 280. In one embodiment, first and second current source/sink circuits 255 and 275, respectively, are combined into a single circuit that is coupled (e.g., multiplexed) to each of the anode of first diode 250, at node 252, and the anode of second diode 270, at node 272. In another embodiment, first and second voltage measurement circuits 260 and 280, respectively, are coupled (e.g., multiplexed) to each of the anode of first diode 250 and the anode of second diode 270.

Defibrillation Lead Impedance Measurement Operation Example 1

Figure 3:
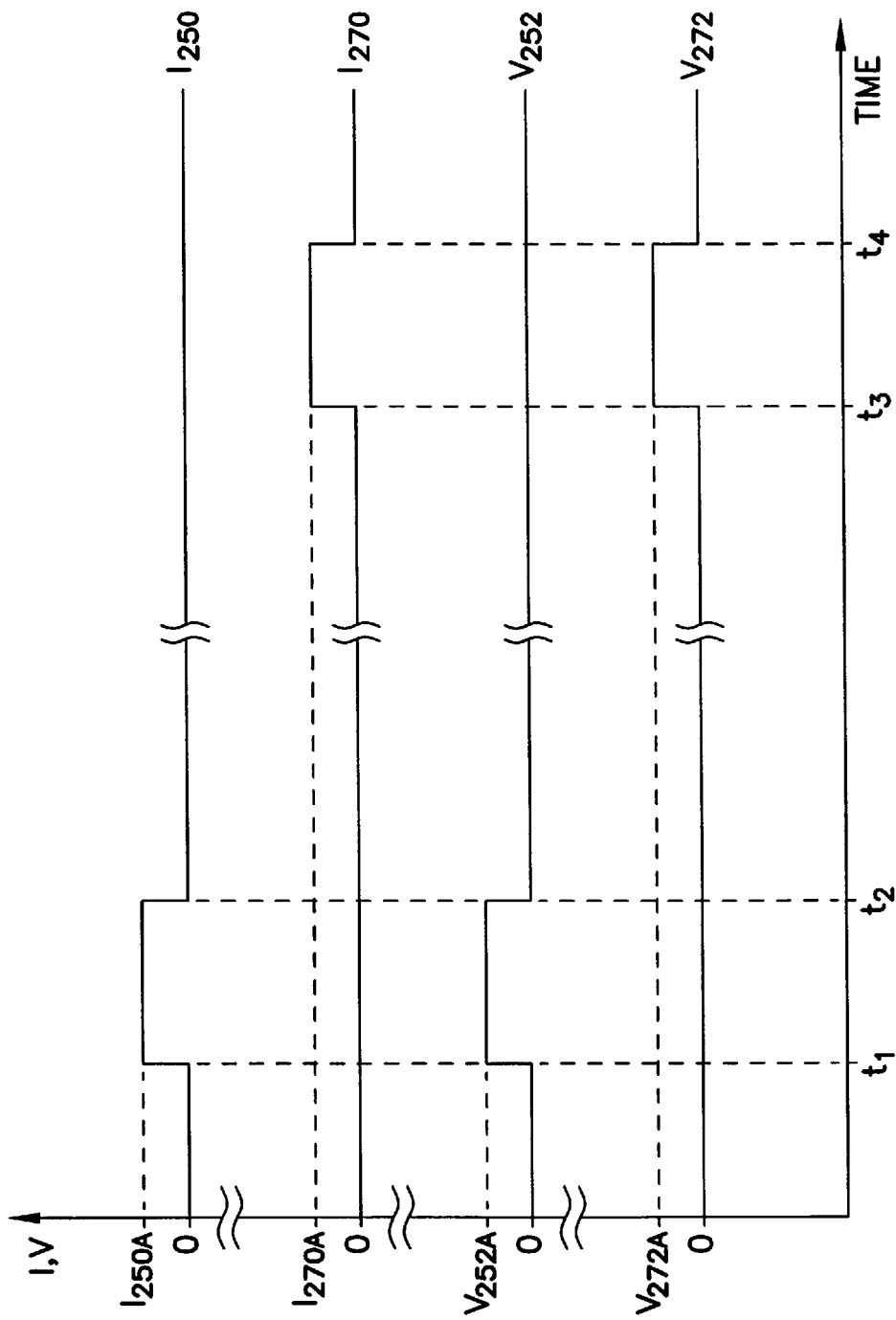
FIG. 3 is a generalized illustration of signal waveforms for a first example of operating a cardiac rhythm management system for performing a defibrillation lead impedance measurement.

FIG. 3 is a generalized signal waveform diagram illustrating generally, by way of example, but not by way of limitation, one embodiment of a technique of operating system 100, such as illustrated in part in FIG. 2, for performing a defibrillation lead impedance measurement. At time, $t_0$, first switch 225, second switch 230, third switch 240, and fourth switch 245 are all turned off, such as by control signals from controller 235.

At approximately time $t_1$, second switch 230 is turned on, and first current source/sink circuit 255 is activated to source a test current $I_{250}$ of predetermined approximately constant magnitude $I^{250A}$ (e.g., approximately between 10 to 20 milliamperes) through first diode 250, first defibrillation electrode 120A, and heart resistance 200. The current $I_{250}$ is received by second defibrillation electrode 120B, second switch 230, and returned through ground node 220. At approximately time $t_2$, first current source/sink circuit 255 and second switch 230 are turned off.

During the time period between $t_1$, and t2, a voltage $V_{252}$ is generated at node 252 in response to the test current $I_{250}$ flowing through an effective series resistance that includes the "on" resistance of first diode 250, the defibrillation leadwire resistance, the first defibrillation electrode 120A resistance, the heart resistance 200, the second defibrillation electrode 120B resistance, and the "on" resistance of second switch 230. In one embodiment, during this time, node 272 is coupled to the ground voltage at node 220 by second current source/sink circuit 275 such that second diode 270 is turned off.

At some time during the time period between $t_1$, and $t_2$, the voltage $V_{252}$ stabilizes and is then sampled by voltage measurement circuit 260, obtaining the measured voltage $V_{252A}$. A first indication of the defibrillation lead impedance, $Z_1$, is obtained by dividing the measured voltage $V_{252}$ by the known current magnitude $I_{250A}$. In this embodiment, $Z_1$, includes the "on" resistances of first diode 250 and second switch 230, as discussed above.

At approximately time $t_3$, first switch 225 is turned on, and second current source/sink circuit 275 is activated to source a test current $I_{270}$ of predetermined magnitude $I_{270A}$ through second diode 270, second defibrillation electrode 120B, and heart resistance 200. The current $I_{270}$ is received by first defibrillation electrode 120A, first switch 225, and returned through ground node 220. At approximately time $t_4$, second current source/sink circuit 275 and first switch 225 are turned off.

During the time period between $t_3$ and $t_4$, a voltage $V_{272}$ is generated at node 272 in response to the test current $I_{270}$ flowing through an effective series resistance that includes the "on" resistance of second diode 270, the defibrillation leadwire resistance, the second defibrillation electrode 120B resistance, the heart resistance 200, the first defibrillation electrode 120A resistance, and the "on" resistance of first switch 225. In one embodiment, during this time, node 252 is coupled to the ground voltage at node 220 by first current source/sink circuit 255 such that first diode 250 is turned off.

According to one aspect of the present technique, the defibrillation lead impedance measurement test currents are approximately "charge-balanced," such that the charge sourced at first electrode 120A during the time period between $t_1$ and $t_2$ is approximately equal to the charge sunk at first electrode 120A during the time period between $t_3$ and $t_4$. Similarly, the charge sunk at second electrode 120B during the time period between $t_1$ and $t_2$ is approximately equal to the charge sourced at second electrode 120B during the time period between $t_3$ and $t_4$. In one embodiment, by way of example, but not by way of limitation, the time period $t_4-t_3$ is approximately equal to the time period $t_2-t_1$, and the test current magnitude $I_{270A}$ is approximately equal to the test current magnitude $I_{250A}$. In a further embodiment, by way of example, but not by way of limitation, $t_4-t_3 \approx t_2-t_1 \approx 10$ to 100 microseconds (e.g., 32 microseconds), $I_{270A} \approx I_{250A} \approx 10$ to 20 milliamperes, and $t_3-t_2 \approx 1.5$ milliseconds. However, it is understood that other time periods or test current levels could also be used.

In a further embodiment, a second defibrillation lead impedance measurement is optionally obtained. In one such example, at some time during the time period between $t_3$ and $t_4$, the voltage $V_{272}$ stabilizes and is then sampled by voltage measurement circuit 280, obtaining the measured voltage $V_{272A}$. A second indication of the defibrillation lead impedance, $Z_2$, is obtained by dividing the measured voltage $V_{272A}$ by the known current magnitude $I_{270A}$. In this embodiment, $Z_2$ includes the "on" resistances of second diode 270 and first switch 225, as discussed above. In one embodiment, the defibrillation lead impedance is determined by averaging $Z_1$ and $Z_2$. However, it is understood that system 100 does not require the use of more than one defibrillation lead impedance measurement.

Defibrillation Lead Impedance Measurement Operation Example 2

Figure 4A:
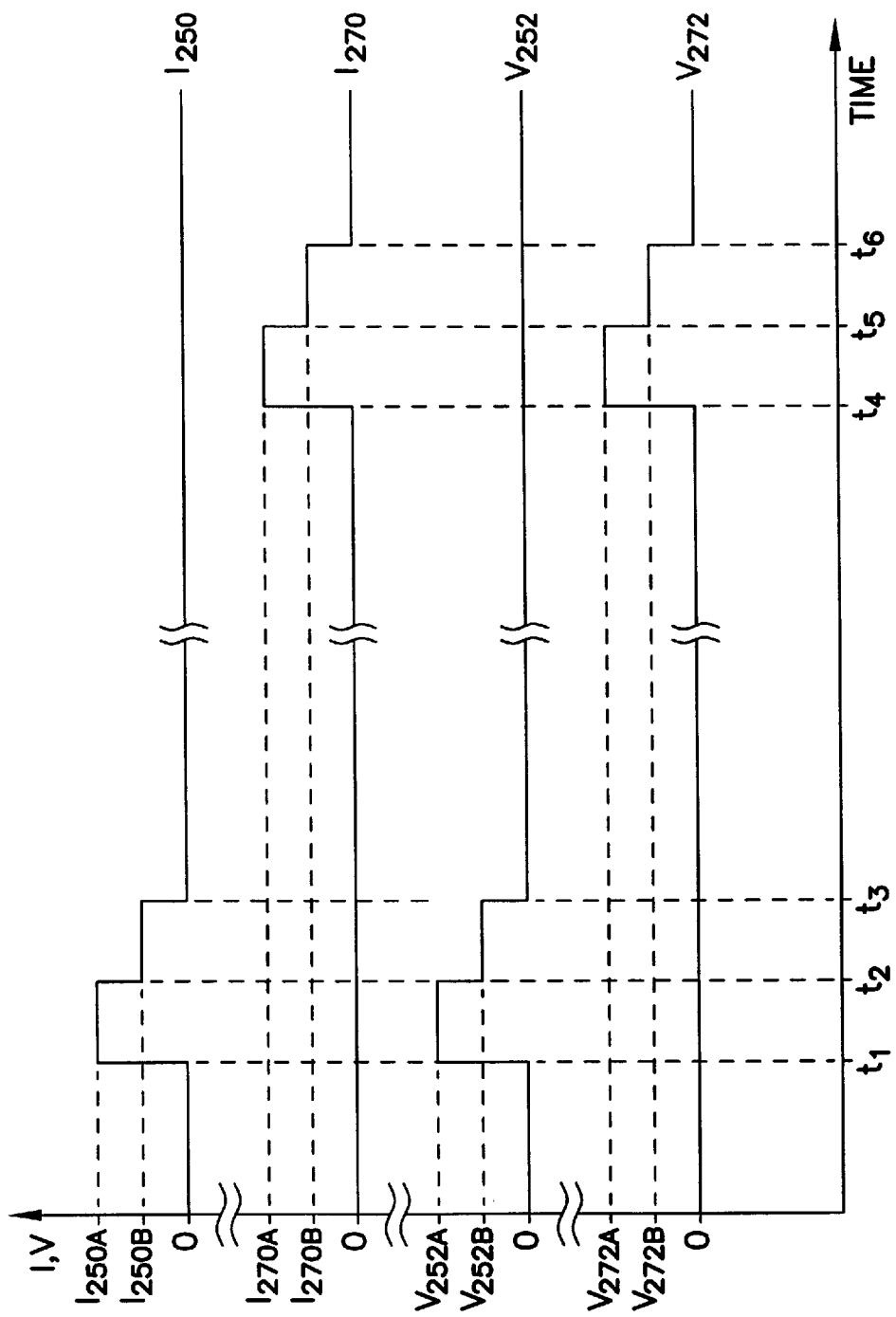
FIG. 4A is a generalized illustration of signal waveforms for a second example of operating a cardiac rhythm management system for performing a defibrillation lead impedance measurement.

FIG. 4A is a generalized signal waveform diagram illustrating generally, by way of example, but not by way of limitation, another embodiment of a technique of operating system 100, such as illustrated in FIG. 2, for performing a defibrillation lead impedance measurement. At time, $t_0$, first switch 225, second switch 230, third switch 240, and fourth switch 245 are all turned off, such as by control signals from controller 235.

At approximately time $t_1$, second switch 230 is turned on, and first current source/sink circuit 255 is activated to source a test current $I_{250}$ of predetermined magnitude $I_{250A}$ through first diode 250, first defibrillation electrode 120A, and heart resistance 200. The current $I_{250}$ is received by second defibrillation electrode 120B, second switch 230, and returned through ground node 220. At approximately time $t_2$, the test current $I_{250}$ sourced by first current source/sink circuit 255 is changed from $I_{250A}$ to a second predetermined magnitude, $I_{250B}$. At approximately time $t_3$, second switch 230 is turned off and first current source/sink circuit 255 is deactivated.

At some time during the time period between $t_1$ and $t_2$, the voltage $V_{252}$ stabilizes and is then sampled by first voltage measurement circuit 260, obtaining first measured voltage $V_{252A}$. Similarly, at some time during the time period between $t_2$ and $t_3$, the voltage $V_{252}$ stabilizes and is then sampled by first voltage measurement circuit 260, obtaining second measured voltage $V_{252B}$. A differential first indication of the defibrillation lead impedance, $Z_{1D}$, is obtained according to Equation 1. In one example, the operations described by Equation 1 are carried out in controller 235 which, in one embodiment, includes a peripheral analog-to-digital (A/D) converter for converting the measured voltage differences into digital values before performing the calculation illustrated by Equation 1.

$$Z_{1D} = \frac{V_{252A} - V_{252B}}{I_{250A} - I_{250B}} \quad (1)$$

In Equation 1, first voltage measurement circuit 260 performs a differential voltage measurement using the two sampled voltages $V_{252A}$ and $V_{252}$. The difference between these two sampled voltages is digitized by the A/D converter. In one embodiment, the difference $I_{250A}-I_{250B}$ is a known difference between predetermined current magnitudes, such that it need undergo measurement and A/D conversion. Instead, the known digital value corresponding to the difference $I_{250A-I250B}$ is stored digitally in device 105, or alternatively in an external programmer, for carrying out the calculation of Equation 1. In another embodiment, the values of $I_{250A}$ and $I_{250B}$ are measured during manufacture of device 105, and these measured values (or the difference between them) are stored digitally in device 105, or alternatively in an external programmer, for use in the calculation of Equation 1. This provides a more accurate measurement because it accounts for variability in the test current amplitudes between particular ones of devices 105.

The current magnitudes $I_{250A}$ and $I_{250B}$ are selected to be sufficiently small as to avoid significant discomfort to the patient (e.g., $I_{250A} \approx 20$ milliamperes and $I_{250B} \approx 10$ milliamperes, or vice-versa). The selected current magnitudes $I_{250A}$ and $I_{250B}$ are sufficiently large so that the series combination of the "on" resistances of first diode 250 and second switch 230 are suitably small (e.g., 5 Ω total series "on" resistance) compared to the smallest expected actual lead impedance (e.g., 15 Ω) of the leadwire and heart. By using the differential lead impedance measurement of Equation 1, the effect of first diode 250 and second switch 230 is canceled or substantially reduced.

At approximately time $t_4$, first switch 225 is turned on, and second current source/sink circuit 275 is activated to source a test current $I_{270}$ of predetermined magnitude $I_{270}A$ through second diode 270, second defibrillation electrode 120B, and heart resistance 200. The current $I_{270}$ is received by second defibrillation electrode 120A, first switch 225, and returned through ground node 220. At approximately time $t_5$, the test current $I_{270}$ sourced by second current source/sink circuit 275 is changed from $I_{270A}$ to a second predetermined magnitude $I_{270B}$. At approximately time $t_6$, first switch 225 is turned off and second current source/sink circuit 275 is deactivated.

According to one aspect of the present technique, the defibrillation lead impedance measurement test currents are approximately "charge-balanced," such that the charge sourced at first electrode 120A during the time period between $t_1$ and $t_3$ is approximately equal to the charge sunk at first electrode 120A (sourced by electrode 120B) during the time period between $t_4$ and $t_6$. In one embodiment, by way of example, but not by way of limitation, $t_6-t_5 \approx t_3-t_2$, and $t_5-t_4 \approx t_2-t_1$, and $I_{270A} \approx I_{250A}$, and $I_{270B} \approx I_{250B}$. In a further embodiment, by way of example, but not by way of limitation, $t_6-t_5 \approx t_3-t_2 \approx 32$ microseconds, and $t_5-t_4 \approx t_2-t_1 \approx 32$ microseconds, and $I_{270A} \approx I_{250A} \approx 20$ milliamperes, and $I_{270B} \approx I_{250B} \approx 10$ milliamperes, and $t_4-t_3 \approx 1.5$ milliseconds. However, it is understood that other time periods or test current levels could also be used.

In one further embodiment, a second differential defibrillation lead impedance measurement is optionally obtained. At some time during the time period between $t_4$ and $t_5$, the voltage $V_{272}$ stabilizes and is then sampled by second voltage measurement circuit 280, obtaining third measured voltage $V_{272A}$. Similarly, at some time during the time period between $t_5$ and $t_6$, the voltage $V_{272}$ stabilizes and is then sampled by second voltage measurement circuit 280, obtaining fourth measured voltage $V_{252B}$. A differential second indication of the defibrillation lead impedance, $Z_{2D}$, is obtained according to Equation 2. In one example, the operations described by Equation 2 are carried out in controller 235 which, in one embodiment, includes a peripheral analog-to-digital (A/D) converter for converting the measured voltage differences into digital values before performing the calculation illustrated by Equation 2.

$$Z_{2D} = \frac{V_{272A} - V_{272B}}{I_{270A} - I_{270B}} \quad (2)$$

In Equation 2, second voltage measurement circuit 280 performs a differential voltage measurement using the two sampled voltages $V_{272A}$ and $V_{272B}$. The difference between these two sampled voltages is digitized by the A/D converter. In one embodiment, the difference $I_{270A}-I_{270B}$ is a known difference between predetermined current magnitudes, such that it need not undergo measurement and A/D conversion. Instead, the known digital value corresponding to the difference $I_{250A}-I_{250B}$ is stored digitally in device 105, or alternatively in an external programmer, for carrying out the calculation of Equation 2. In another embodiment, the values of $I_{270A}$ and $I_{270B}$ are measured during manufacture of device 105, and these measured values (or the difference between them) are stored digitally in device 105, or alternatively in an external programmer, for use in the calculation of Equation 2. This provides a more accurate measurement because it accounts for variability in the test current amplitudes between particular ones of devices 105.

The current magnitudes $I_{270A}$ and $I_{270B}$ are selected to be sufficiently small as to avoid significant discomfort to the patient (e.g., $I_{270A} \approx 20$ milliamperes and $I_{270B} \approx 10$ milliamperes, or vice-versa). The selected current magnitudes $I_{270A}$ and $I_{270B}$ are sufficiently large so that the "on" resistances of second diode 270 and first switch 225 are suitably small (e.g., 5 Ω total series "on" resistance) compared to the smallest expected actual lead impedance (e.g., 15 Ω) of the leadwire and heart. By using the differential defibrillation lead impedance measurement of Equation 2, the effect of second diode 270 and first switch 225 is canceled or substantially reduced. In this embodiment, the defibrillation lead impedance, $Z_M$, is determined by averaging $Z_{1D}$ and $Z_{2D}$. This advantageously minimizes effects on the defibrillation lead impedance measurement resulting from the different directions of the test current through $R_{200}$ during the two separate defibrillation lead impedance measurements. However, it is understood that system 100 does not require the use of more than one defibrillation lead impedance measurement.

Figure 4B:
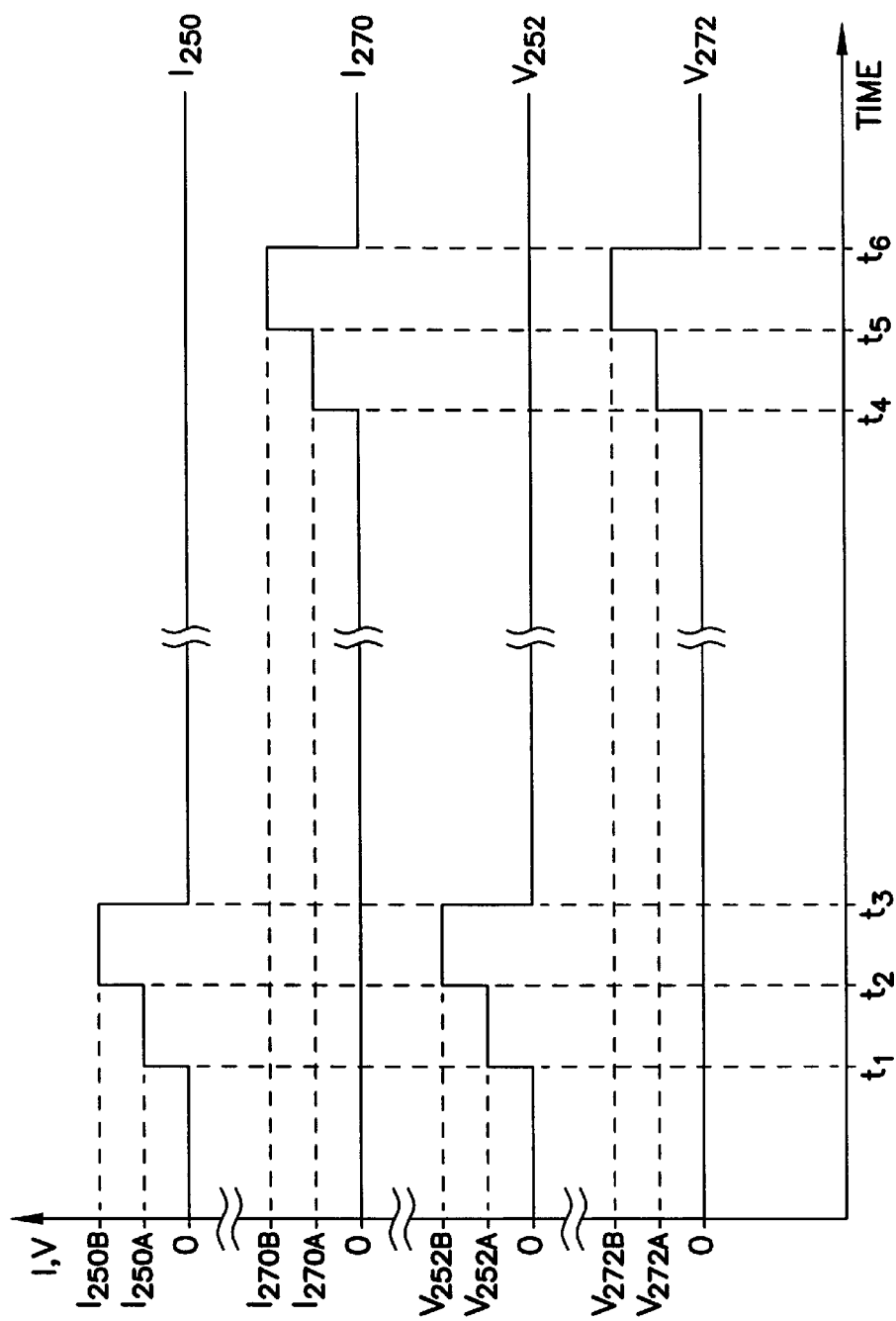
FIG. 4B is a generalized illustration of signal waveforms for a second example of operating a cardiac rhythm management system for performing a defibrillation lead impedance measurement.

FIG. 4B is a generalized waveform diagram, similar to FIG. 4A, illustrating a reversal in the relative relationship of the test current amplitudes $I_{250A}$ and $I_{250B}$, $I_{270A}$ and $I_{270B}$, and in the amplitude relationship of the resulting measured voltages $V_{252A}$ and $V_{252B}$, and $V_{272A}$ and $V_{272B}$. Operation of system 100 as illustrated in FIG. 4B, is analogous to its operation described with respect to FIG. 4A. A first differential impedance measurement is obtained as described in Equation 1, and a second differential impedance measurement is optionally obtained, such as described in Equation 2.

Defibrillation Lead Impedance Measurement
Hardware Example 2

Figure 5:
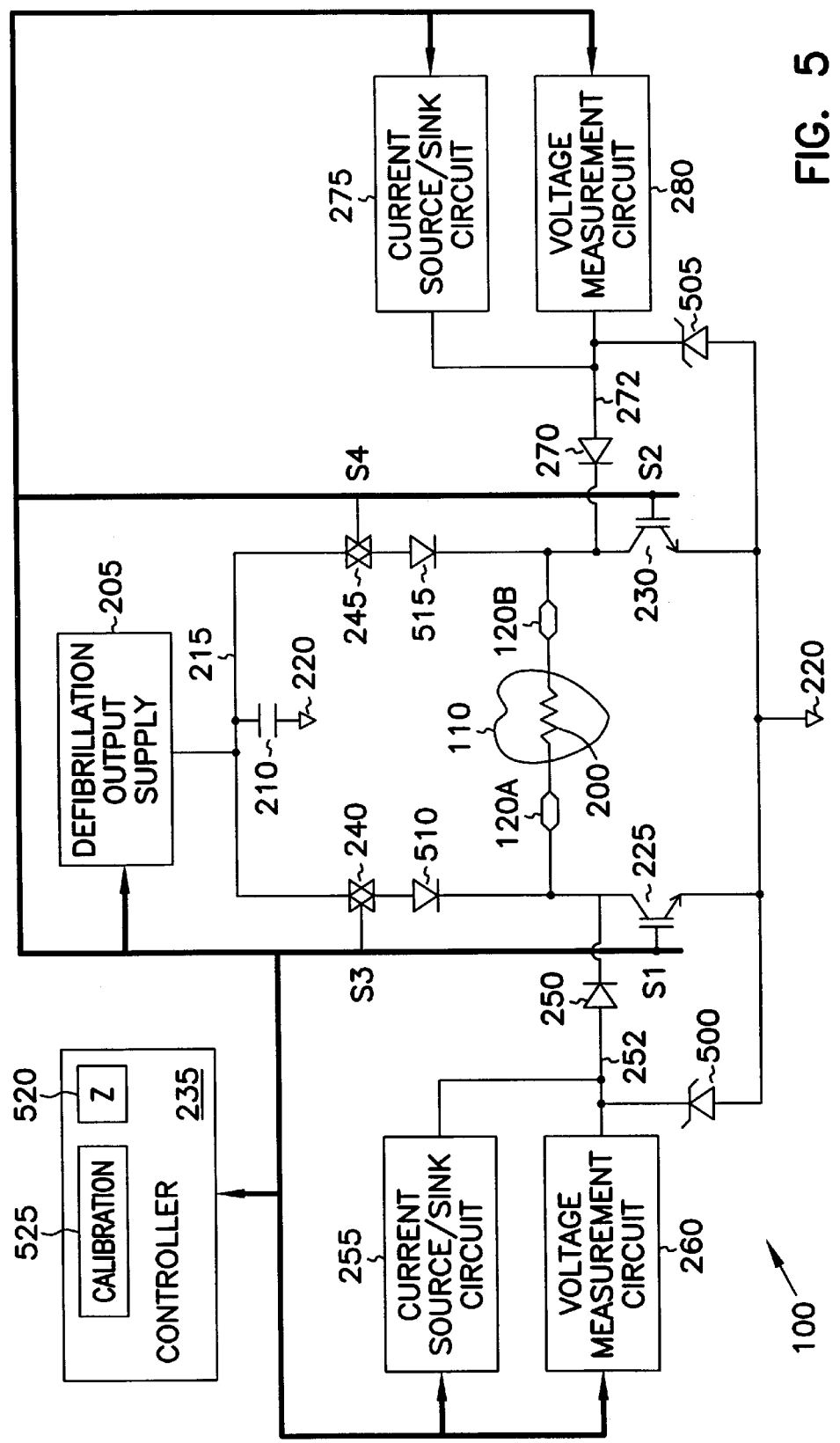
FIG. 5 is a generalized schematic/block diagram illustrating a second example of portions of the cardiac rhythm management system for measuring lead impedance, the second example including additional diodes protecting switching devices and measurement circuits.

FIG. 5 is a generalized schematic/block diagram illustrating generally, by way of example, but not by way of limitation another embodiment of portions of system 100. FIG. 5 is similar to FIG. 2 in many respects. FIG. 5 includes, however, a first zener diode 500 including an anode coupled to ground node 220 and a cathode coupled to the anode of first diode 250 at node 252. A second zener diode 505 includes an anode coupled to ground node 220 and a cathode coupled to the anode of second diode 270 at node 272.

First zener diode 500 protects first current source/sink circuit 255 and first voltage measurement circuit 280 from dangerously large positive and/or negative voltages at node 252, such as during a defibrillation countershock delivered to heart 110 by system 100 or by an external defibrillator. During such a defibrillation countershock delivered by system 100, for example, first zener diode 500 clamps node 252 at a safe voltage (i.e., at approximately the reverse breakdown voltage of first zener diode 500) and ensures that first diode 250 remains off. Moreover, if a sufficiently large negative voltage is present at first defibrillation electrode 120A, such as during a defibrillation countershock delivered by an external defibrillator, for example, first diode 250 and first zener diode 500 each turn on. This clamps the voltage at first defibrillation electrode 120A (i.e., at a negative voltage that is equal to the series "on" voltage of first diode 250 and first zener diode 500), thereby protecting first switch 225 against dangerously large negative voltages. This also clamps the voltage at node 252 (i.e., at a negative voltage that is equal to the "on" voltage of first zener diode 500), thereby protecting first current source/sink 255 and first voltage measurement circuit 260 against dangerously large negative voltages. Second zener diode 505 operates analogously to first zener diode 500, protecting second current source/sink circuit 275 and first voltage measurement circuit 280 from dangerously large positive and/or negative voltages at nodes 272, and protecting second switch 230 from dangerously large negative voltages at second defibrillation electrode 120B.

FIG. 5 also illustrates third diode 510 and fourth diode 515. Third diode 510 includes an anode that is coupled to third switch 240 and a cathode that is coupled to first defibrillation electrode 120A. Fourth diode 515 includes an anode that is coupled to fourth switch 245 and a cathode that is coupled to second defibrillation electrode 120B. According to one aspect of system 100, third diode 510 in series with third switch 240 provides a greater series voltage handling capability than does third switch 240 alone, i.e., without third diode 510. Similarly, fourth diode 515 in series with fourth switch 245 provides a greater series voltage handling capability than does fourth switch 245 alone, i.e., without fourth diode 515.

FIG. 5 also illustrates a lead impedance module 520 and a calibration module 525. The lead impedance module 520 and calibration module 525 are included within controller 235, or alternatively located in an external programmer that is not implanted in the patient, but is communicatively coupled to the implanted device 105. In one embodiment, the lead impedance module 520 and calibration module 525 are implemented as a sequence of operative steps carried out on a microprocessor, for respectively performing a differential lead impedance measurement, as discussed above, and a calibration of the measured lead impedance using measured values of known resistances, as discussed below.

Defibrillation Lead Impedance Measurement
Hardware Example 3

Figure 6:
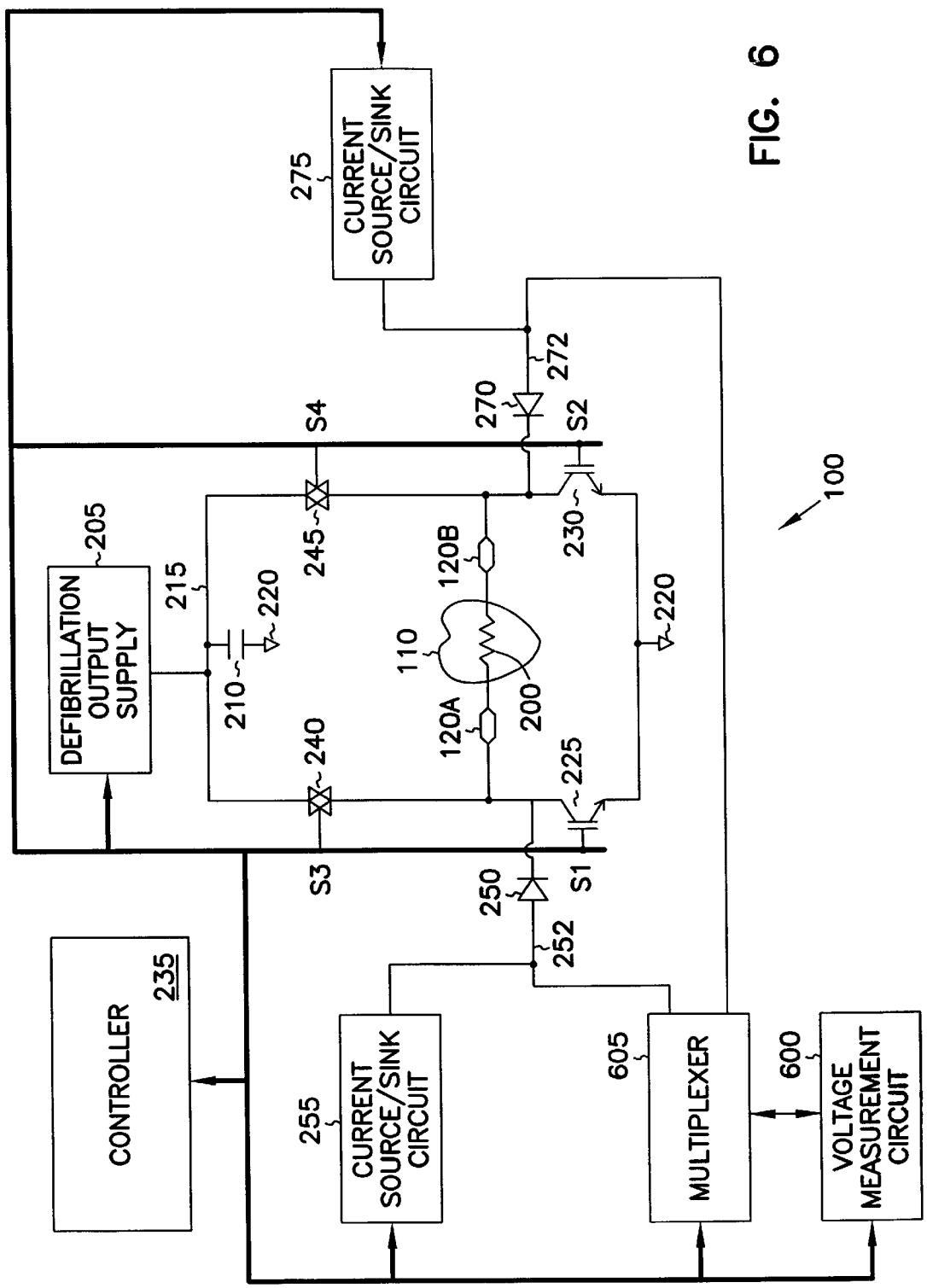
FIG. 6 is a generalized schematic/block diagram illustrating a third example of portions of the cardiac rhythm management system for measuring lead impedance, the third example including a voltage measurement circuit that is multiplexed to more than one defibrillation electrode.

FIG. 6 is a generalized schematic/block diagram illustrating generally, by way of example, but not by way of limitation another embodiment of portions of system 100. FIG. 6 is similar to FIG. 2 in many respects. FIG. 6 includes, however, a single voltage measurement circuit 600, providing the combined functions of first and second voltage measurement circuits 260 and 280, respectively. Nodes 252 and 272 are time-multiplexed by multiplexer 605 to voltage measurement circuit 600 for measuring the voltages at each of nodes 252 and 272, respectively.

Defibrillation Lead Impedance Measurement
Hardware Example 4

Figure 7:
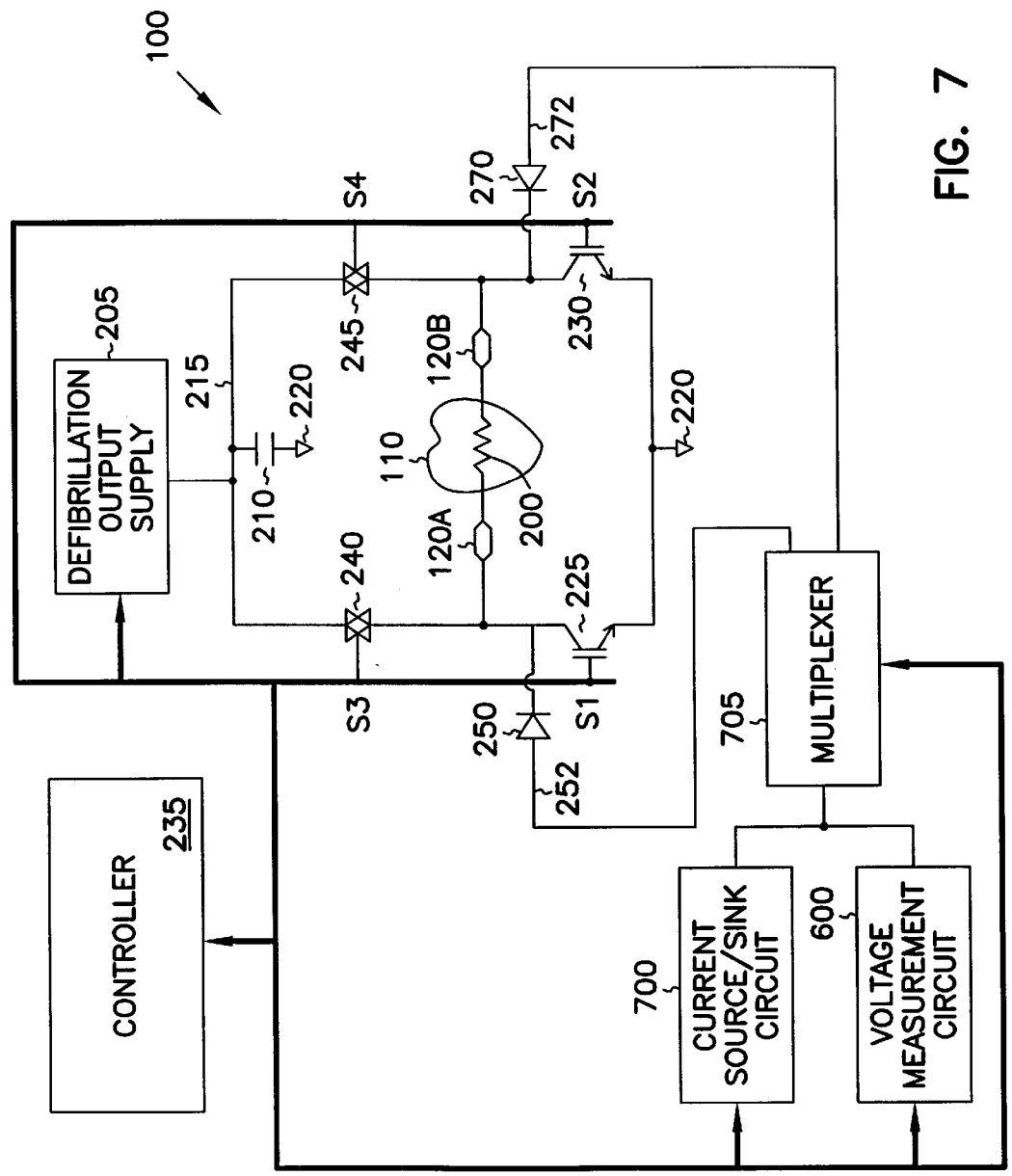
FIG. 7 is a generalized schematic/block diagram illustrating a fourth example of portions of the cardiac rhythm management system for measuring lead impedance, the fourth example including a shared multiplexer for multiplexing a current source/sink circuit and a voltage measurement circuit to more than one defibrillation electrode.

FIG. 7 is a generalized schematic/block diagram illustrating generally, by way of example, but not by way of limitation another embodiment of portions of system 100. FIG. 7 is similar to FIG. 2 in many respects. FIG. 7 includes, however, a single voltage measurement circuit 600, providing the combined functions of first and second voltage measurement circuits 260 and 280, respectively. FIG. 7 also includes a single current source/sink circuit 700, providing the combined functions of first and second current source/sink circuits 255 and 275, respectively. Nodes 252 and 272 are time-multiplexed by multiplexer 705 to current source/sink circuit 700 and voltage measurement circuit 600 for providing a test current to and measuring the voltages at each of nodes 252 and 272, respectively.

Defibrillation Lead Impedance Measurement
Hardware Example 5

Figure 8:
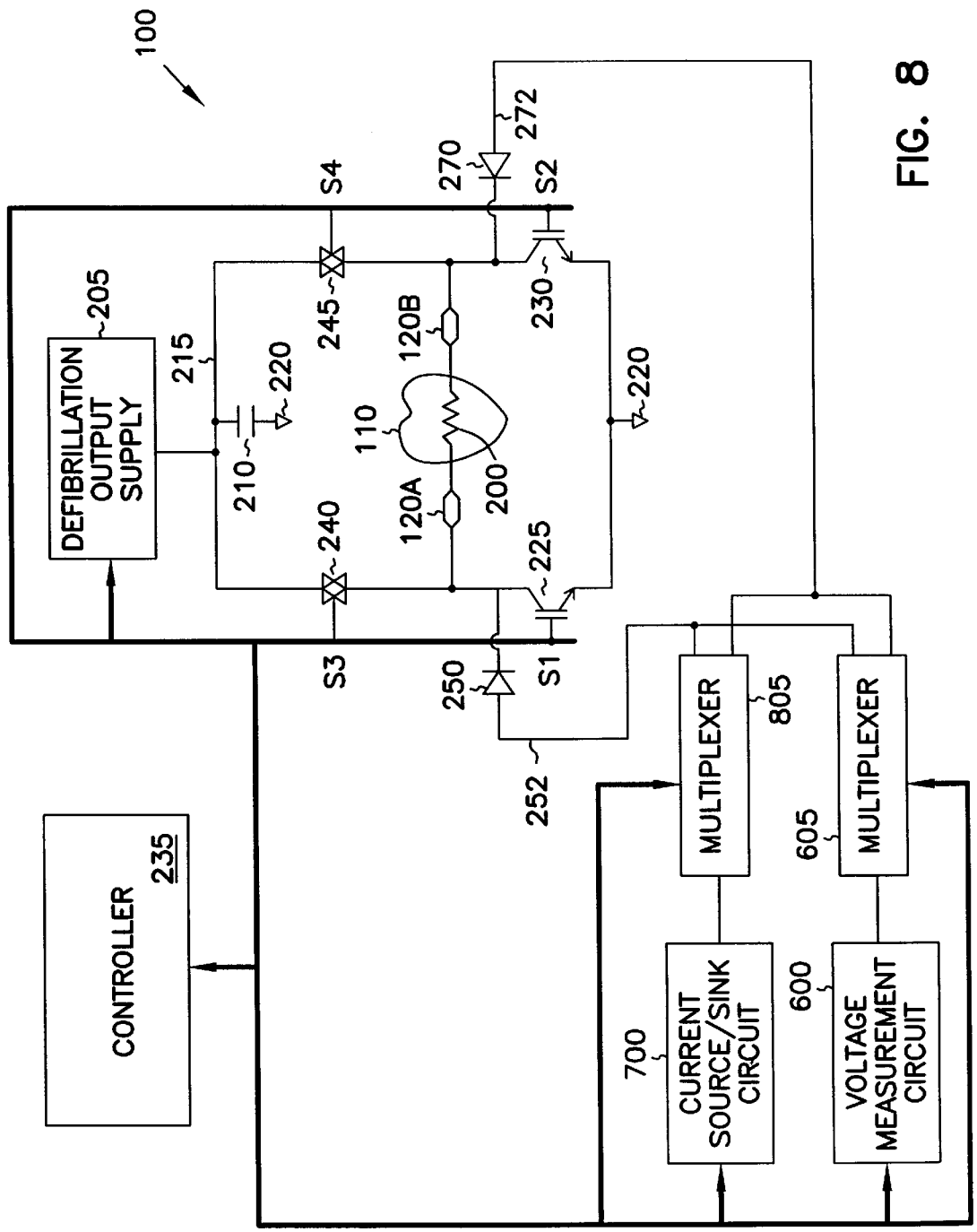
FIG. 8 is a generalized schematic/block diagram illustrating a fifth example of portions of the cardiac rhythm management system for measuring lead impedance, the fifth example including separate multiplexers for multiplexing a current source/sink circuit and a voltage measurement circuit to more than one defibrillation electrode.

FIG. 8 is a generalized schematic/block diagram illustrating generally, by way of example, but not by way of limitation another embodiment of portions of system 100. FIG. 8 is similar to FIG. 2 in many respects. FIG. 8 includes, however, a single voltage measurement circuit 600, providing the combined functions of first and second voltage measurement circuits 260 and 280, respectively. FIG. 8 also includes a single current source/sink circuit 700, providing the combined functions of first and second current source/sink circuits 255 and 275, respectively. Nodes 252 and 272 are time-multiplexed by multiplexer 605 to voltage measurement circuit 600 for measuring the voltages at each of nodes 252 and 272, respectively. Nodes 252 and 272 are time-multiplexed by multiplexer 805 to current source/sink circuit 700 for providing a test current to each of nodes 252 and 272, respectively.

Test Current Source/Sink Circuit Example

Figure 9:
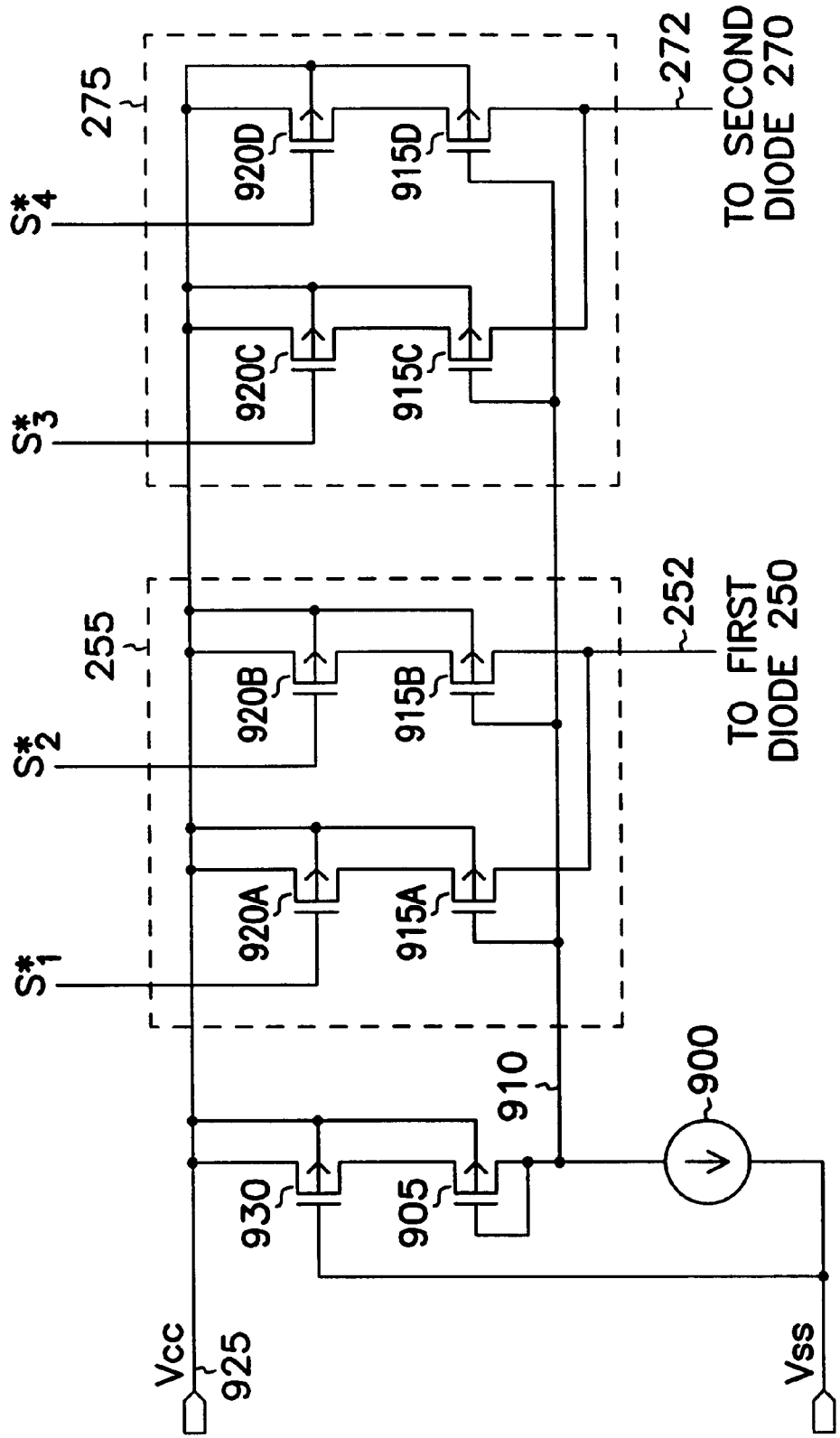
FIG. 9 is a generalized schematic/block diagram illustrating one embodiment of current source/sink circuit and associated circuits.

FIG. 9 is a generalized schematic/block diagram illustrating generally, by way of example, but not by way of limitation one embodiment of first current source/sink circuit 255, second current source/sink circuit 275, and associated circuits for operating system 100 according to the signal waveforms illustrated in FIGS. 4A–B. An input reference current 900 is provided to diode-connected transistor 905, which produces a current mirror voltage at node 910 that is received by current mirror transistors 915A–D. Switching transistors 920A–D are individually interposed between each of the current mirror transistors 915A–D and the positive power supply $V_{CC}$ at node 925. Transistor 930 is interposed between diode-connected transistor 905 and the positive power supply $V_{CC}$ at node 925 such that diode-connected transistor 905 has a resistance at its source terminal that is similar to that at the source terminals of each of the current mirror transistors 915A–D. In this example embodiment, transistors 905, 915A–D, 920A–D, and 930 are all p-channel metal-oxide-semiconductor (PMOS) field-effect transistors (FETs) having lightly-doped drain regions for withstanding high drain voltages (e.g., at least up to the reverse breakdown voltage of zener diodes 500 and 505).

When system 100 is operated as illustrated in FIG. 4A, switches 920A–D are operated as described below. Before time $t_1$, switches 920A–D are all off, $S_1^*=S_2^*=S_3^*=S_1^*=V_{CC}$=(high). At time $t_1$, switches 920A and 920B are turned on (i.e., $S_1^*=S_2^*=V_{SS}$=(low)), such that current mirror transistors 915A–B together source a test current of amplitude $I_{250A}$ to first defibrillation electrode 120A. At time $t_2$, switch 920A is turned off (i.e., $S_1^*$=high, and $S_2^*$=low), such that current mirror transistor 915B alone sources a test current of amplitude $I_{250B}$ to first defibrillation electrode 120A. At time $t_3$, switch 920B is turned off (i.e., $S_1^*=S_2^*=S_3^*=S_1^*$=high); interrupting the test current to first defibrillation electrode 120A. At time $t_4$, switches 920C and 920D are turned on (i.e., $S_3^*=S_4^*$=low), such that current mirror transistors 915C–D together source a test current of amplitude 270A to second defibrillation electrode 120B. At time $t_5$, switch 920C is turned off (i.e., $S_3^*$=high, and $S_4^*$=low), such that current mirror transistor 915D alone sources a test current of amplitude $I_{270B}$ to second defibrillation electrode 120B. At time $t_6$, switch 920D is turned off (i.e., $S_1^*=S_2^*=S_3^*=S_1^*=$high), interrupting the test current to second defibrillation electrode 120B.

When system 100 is operated as illustrated in FIG. 4B, switches 920A–D are operated as described below. Before time $t_1$, switches 920A–D are all off, $S_1^*=S_2^*=S_3^*=S_1^*=V_{CC}$=(high). At time $t_1$, switch 920A is turned on (i.e., $S_1^*$=low), such that current mirror transistor 915A alone sources a test current of amplitude $I_{250A}$ to first defibrillation electrode 120A. At time $t_2$, switch 920B is turned on (i.e., $S_1^*=S_2^*$=low), such that current mirror transistors 915A–B together source a test current of amplitude $I_{250B}$ to first defibrillation electrode 120A. At time $t_3$, switches 920A–B are turned off (i.e., $S_1^*=S_2^*=S_3^*=S_1^*$=high); interrupting the test current to first defibrillation electrode 120A. At time $t_4$, switch 920C is turned on (i.e., $S_3^*$=low), such that current mirror transistor 915C alone sources a test current of amplitude $I_{270A}$ to second defibrillation electrode 120B. At time $t_5$, switch 920D is turned on (i.e., $S_3^*=S_4^*$=low), such that current mirror transistors 915C–D together source a test current of amplitude $I_{270B}$ to second defibrillation electrode 120B. At time $t_6$, switches 920C–D are turned off (i.e., $S_1^*=S_2^*=S_3=S_1^*$=high), interrupting the test current to second defibrillation electrode 120B.

Voltage Measurement Circuit Example

Figure 10:
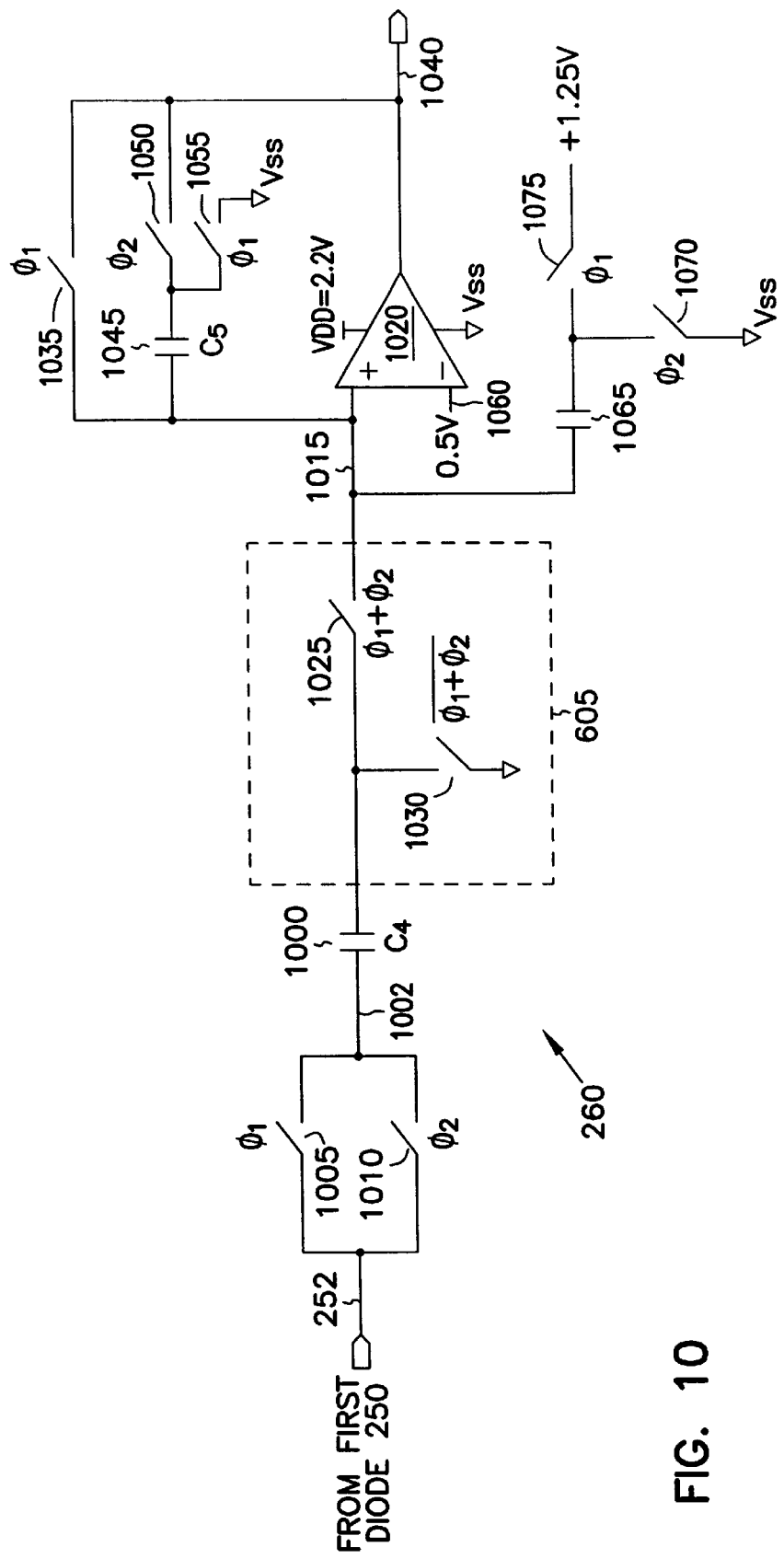
FIG. 10 is a generalized schematic diagram illustrating generally one embodiment of a voltage measurement circuit.

FIG. 10 is a generalized schematic diagram illustrating generally, by way of example, but not by way of limitation, one embodiment of a switched-capacitor voltage measurement circuit 260, which operates in conjunction with a current source/sink circuit 255, such as illustrated in FIG. 9, to perform a defibrillation lead impedance measurement.

The voltage measurement circuit 260 includes a sampling capacitor 1000, having a capacitance value $C_4$. A first terminal of sampling capacitor 1000 at node 1002 is coupled via a first input switch 1005 and a second input switch 1010 to node 252. A second terminal of sampling capacitor 1000 is coupled to an inverting input node 1015 of operational amplifier 1020 via a multiplexer 605, only a portion of which is illustrated in FIG. 10. The illustrated portion of multiplexer 605 includes a series multiplexer switch 1025 and a shunt multiplexer switch 1030. An autozero switch 1035 is coupled between inverting input node 1015 and output node 1040 of operational amplifier 1020. Integration capacitor 1045, having a capacitance value $C_5$, includes a first terminal that is coupled to inverting input node 1015. Integration capacitor 1045 includes a second terminal that is coupled to output node 1040 via feedback switch 1050. The second terminal of integration capacitor 1045 is also coupled to ground node $V_{SS}$ via grounding switch 1055. A positive input node 1060 of operational amplifier 1020 is coupled to a stable reference voltage, such as 0.5 volts. An offset capacitor 1065 includes a first terminal that is coupled to inverting input node 1015. A second terminal of offset capacitor 1065 is coupled to ground node $V_{SS}$ via switch 1070. The second terminal of offset capacitor 1065 is also coupled to a stable reference voltage, such as 1.25 volts, via switch 1075.

Operation of system 100 according to FIGS. 2, 4A, 9 and 10 is described below. During the time period $t_2-t_1$ (i.e., $\phi_1$), a first voltage measurement is performed. The voltage at node 252 resulting from first test current level $I_{250A}$ is sampled onto sampling capacitor 1000. Series multiplexer switch 1025 is on and shunt multiplexer switch 1030 is off. Autozero switch 1035 is on and the input offset voltage of operational amplifier 1020 is stored on feedback capacitor 1045. Offset capacitor 1065 is coupled to the 1.25 volt reference voltage. The voltage at output node 1040 is not valid during this time period.

During the time period $t_3-t_2$ (i.e., $\phi_2$), a second voltage measurement is performed. The voltage at node 252 resulting from second test current level $I_{250B}$ is sampled onto sampling capacitor 1000. Because the shunt multiplexer switch 1030 is off and the series multiplexer switch 1025 is on, the resulting change in charge on sampling capacitor 1000 flows through inverting input node 1015 and is stored on integration capacitor 1045 (autozero switch 1035 is off and feedback switch 1050 is on). Because sampling capacitor 1000 already included a stored charge resulting from the first voltage measurement, the voltage at output node 1040 represents the difference between the first and second voltage measurements. Because offset capacitor 1065 is switched from 1.25 volts to ground voltage $V_{SS}$, at time $t_2$, a constant positive dc offset voltage is also introduced at output node 1040 of operational amplifier 1020. The introduced positive offset voltage at output node 1040 keeps operational amplifier 1020 within its dynamic operating range.

In one embodiment, a separate second voltage measurement circuit 280, similar to the circuit illustrated in FIG. 10, is used to perform a differential voltage measurement of the voltage at node 272 during time periods $t_5-t_4$ (i.e., $\phi_1$) and $t_6-t_5$ (i.e., $\phi_2$), as illustrated in FIG. 4A. In another embodiment, a combined voltage measurement circuit 600 is used to perform differential voltage measurements of each of nodes 252 and 272, as illustrated in FIG. 11.

Figure 11:
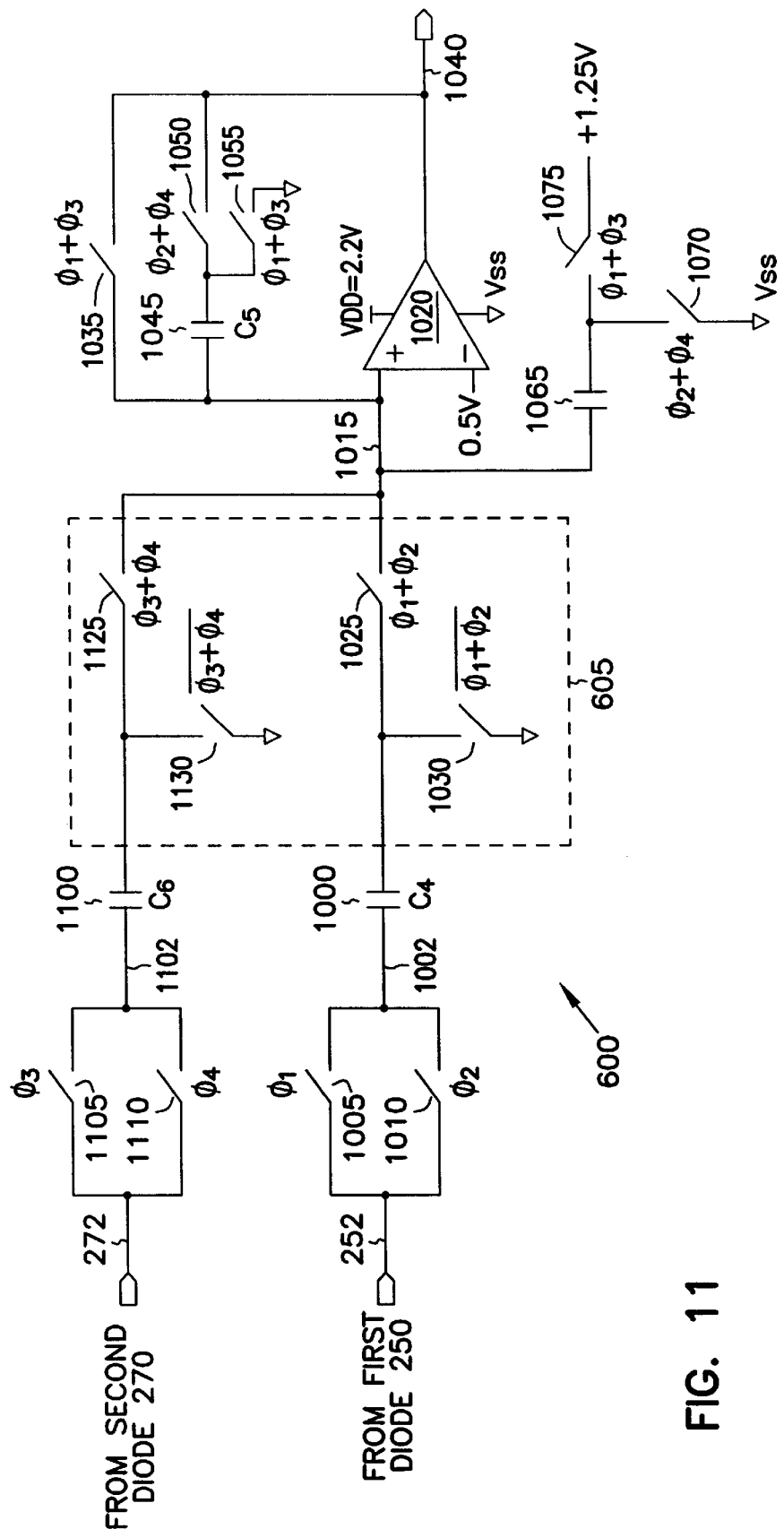
FIG. 11 is a generalized schematic diagram illustrating generally another embodiment of a voltage measurement circuit.

FIG. 11 is a generalized schematic diagram illustrating generally, by way of example, but not by way of limitation, one embodiment of a switched-capacitor voltage measurement circuit 600, similar to the circuit illustrated in FIG. 10, but time multiplexed by multiplexer 605 to each of nodes 252 and 272 for performing first and second voltage measurements at node 272 and third and fourth voltage measurements at node 272. Operational amplifier 1020, integration capacitor 1045, and offset capacitor 1065 and associated circuits are shared for both voltage measurements.

For measuring the voltage at node 272, a separate sampling capacitor 1100 is provided, having a capacitance value $C_6$. A first terminal of sampling capacitor 1100 at node 1102 is coupled via a first input switch 1105 and a second input switch 1110 to node 272. A second terminal of sampling capacitor 1100 is coupled to an inverting input node 1015 of operational amplifier 1020 via multiplexer 605, which includes a series multiplexer switch 1125 and a shunt multiplexer switch 1130.

Voltage measurement circuit 600 operates similarly to voltage measurement circuit 260, described with respect to FIG. 10. However, voltage measurement circuit 600 performs a lead impedance measurement at node 272, in addition to the lead impedance measurement performed at node 252.

Operation of system 100 according to FIGS. 2, 4A, 9 and 11 is described below. During the time period $t_2-t_1$ (i.e., $\phi_1$) a first voltage measurement is performed at node 252, as described with respect to FIG. 10. During the time period $t_3-t_2$ (i.e., $\phi_2$), a second voltage measurement is performed at node 252, as described with respect to FIG. 10.

During the time period $t_5-t_4$ (i.e., $\phi_3$), a third voltage measurement is performed, at node 272, resulting from third test current level $I_{270A}$. The voltage at node 272 is sampled onto sampling capacitor 1100. Series multiplexer switch 1125 is on and shunt multiplexer switch 1130 is off. Autozero switch 1035 is on and the input offset voltage of operational amplifier 1020 is stored on feedback capacitor 1045. Offset capacitor 1065 is coupled to the 1.25 volt reference voltage. The voltage at output node 1040 is not valid during this time period.

During the time period $t_6-t_5$ (i.e., $\phi_4$), a fourth voltage measurement is performed. The voltage at node 272, resulting from fourth test current level $I_{270B}$, is sampled onto sampling capacitor 1100. Because the shunt multiplexer switch 1130 is off and the series multiplexer switch 1125 is on, the resulting change in charge on sampling capacitor 1100 flows through inverting input node 1015 and is stored on integration capacitor 1045 (autozero switch 1035 is off and feedback switch 1050 is on). Because sampling capacitor 1100 already included a stored charge resulting from the third voltage measurement, the voltage at output node 1040 represents the difference between the third and fourth voltage measurements.

Calibration/Correction Example

In one embodiment, the lead impedance measurement circuitry in device 105 is calibrated during manufacturing to improve the precision of the measurement of defibrillator lead impedance. According to one such calibration technique, two different calibration resistances of known values (e.g., $R_1$=30 Ω and $R_2$=80 Ω) are measured as $Z_{1M}$ and $Z_{2M}$, respectively, using one of the above-described defibrillation lead impedance measurement circuits and methods. Controller 235 performs a calibration/correction according to Equation 3 to obtain a corrected measured value, $Z_{CM}$, of an unknown defibrillation lead impedance from its measured value, $Z_M$, the measured values of the known resistances, $Z_{1M}$ and $Z_{2M}$, and the known values of the calibration resistances, $R_1$ and $R_2$.

$$Z_{CM} = R_1 + \frac{Z_{2M} - Z_{1M}}{R_2 - R_1}(Z_M - Z_{1M}) \tag{3}$$

Equation 3 represents one form of performing a point-slope calibration. There are many other possible techniques of performing point-slope calibrations, and such other particular implementations are included within the scope of the present system. In one embodiment, for example, the calibration is performed using the measured voltage differences in Equations 1 and 2 without undergoing the computational step of converting the measured voltage differences into corresponding impedances. Furthermore, it is understood that calibration/correction is performed either in the implanted device 105, or is alternatively performed in an external programmer operating on data that is communicatively coupled from the implanted device 105 to the external programmer.

Conclusion

The above-described cardiac rhythm management system provides, among other things, a defibrillation lead impedance measurement system. Instead of measuring defibrillation lead impedance by delivering a high energy or low energy defibrillation countershock and measuring a resulting voltage, defibrillation lead impedance is measured using a test current source that is different from the defibrillation output supply. A voltage resulting from the test current flowing through the defibrillation lead and heart resistance is measured. The defibrillation lead impedance is determined from the measured voltage.

Because low amplitude test current pulses are used (e.g., 10–20 milliamperes), the defibrillation lead impedance measurement does not cause significant pain or discomfort to the patient, nor will it result in capture of the heart and resulting cardiac depolarizations. As a result, the defibrillation lead impedance can be measured routinely for diagnostic or other purposes.

In one embodiment, the test currents are charge-balanced, i.e., a first test current pulse waveform sourced at a particular defibrillation electrode is offset by a substantially equal amount of charge sunk at that defibrillation electrode by a second test current pulse waveform, because the first and second test currents flow in opposite directions. This avoids charge build-up in the heart that may increase the difficulty of sensing intrinsic electrical heart activity signals. It also avoids degeneration of the defibrillation electrodes by electroplating or corrosion.

One embodiment provides test current pulses of at least two different steady-state amplitude steps. Defibrillation lead impedance is determined differentially by measuring a voltage associated with each test current amplitude step, and dividing a difference of the measured voltage by a corresponding difference in the test current amplitudes. This technique allows cancellation of a component of the measured voltage that is not associated with the desired defibrillation lead measurement. Another embodiment provides bidirectional test currents to account for polarity effects on the defibrillation lead impedance measurement. A further embodiment provides a calibration/correction technique in which measurements of known resistances are used to correct a measurement of an unknown defibrillation lead impedance measurement.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method of determining an impedance between first and second defibrillation electrodes, the method comprising:
   delivering a first current, for a first time period, from the first defibrillation electrode to the second defibrillation electrode;
   delivering a second current, for a second time period, from the second defibrillation electrode to the first defibrillation electrode, wherein a first charge delivered from the first defibrillation electrode during the first time period is approximately equal in magnitude to a second charge delivered from the second defibrillation electrode during the second time period; and
   measuring a voltage associated with the first and second defibrillation electrodes while at least one of the first and second currents is being delivered.

2. The method of claim 1, in which delivering the first and second currents includes using the first and second time periods that are approximately equal.

3. The method of claim 1, in which delivering the first and second currents includes using the first and second current s that are approximately equal in magnitude.

4. The method of claim 1, in which delivering the first current includes delivering first and second current levels, and the first current level is different from the second current level.

5. The method of claim 4, in which measuring the voltage includes:
   measuring a first voltage associated with the first current level; and measuring a second voltage associated with the second current level.

6. The method of claim 5, further comprising obtaining a first indication of the impedance from a quotient of a difference between the first and second voltage measurements and a difference between the first and second current levels.

7. The method of claim 6, in which delivering the second current includes delivering third and fourth current levels, and the third current level is different from the fourth current level.

8. The method of claim 7, in which measuring the voltage further includes:
   measuring a third voltage associated with the third current level; and
   measuring a fourth voltage associated with the fourth current level.

9. The method of claim 8, further comprising obtaining a second indication of the impedance from a quotient of the difference between the third and fourth voltage measurements and a difference between the third and fourth current levels.

10. The method of claim 9, further comprising obtaining a third indication of the impedance based on an average value of the first and second indications of the impedance.

11. The method of claim 1, further comprising:
   measuring a first known impedance by delivering the first and second currents and measuring the voltage associated with the first and second defibrillation electrodes;
   measuring a second known impedance, which is different in value from the first known impedance, by delivering the first and second currents and measuring the voltage associated with the first and second defibrillation electrodes;
   measuring a third unknown impedance, by delivering the first and second currents and measuring the voltage associated with the first and second defibrillation electrodes; and
   adjusting the third unknown impedance measurement based on the first and second known impedance measurements.

12. A method of determining an impedance between first and second defibrillation electrodes, the method comprising:
   sourcing a first current, for a first time period, at the first defibrillation electrode;
   sinking a second current, for a second time period, at the first defibrillation electrode, wherein a first charge sourced at the first defibrillation electrode during the first time period is approximately equal in magnitude to a second charge sunk at the first defibrillation electrode during the second time period; and
   measuring a voltage associated with the first and second defibrillation electrodes while at least one of the first and second currents is being delivered.

13. An apparatus for determining an impedance between first and second defibrillation electrodes, the apparatus comprising:
   means for delivering a first current, for a first time period, from the first defibrillation electrode to the second defibrillation electrode;

means for delivering a second current, for a second time period, from the second defibrillation electrode to the first defibrillation electrode, wherein a first charge delivered from the first defibrillation electrode during the first time period is approximately equal in magnitude to a second charge delivered from the second defibrillation electrode during the second time period; and means for measuring a voltage associated with the first and second defibrillation electrodes while at least one of the first and second currents is being delivered.

14. An apparatus for determining an impedance between first and second defibrillation electrodes, the apparatus comprising:

a first current source/sink circuit coupled to the first defibrillation electrode;

a first voltage measurement circuit coupled to the first defibrillation electrode;

a second current source/sink circuit coupled to the second defibrillation electrode;

a controller, providing control signals to the first and second current source/sink circuits for sourcing a first charge at the first electrode and sinking a second charge at the first electrode, wherein the first and second charges are approximately equal in magnitude.

15. The apparatus of claim 14, wherein the controller provides at least one control signal to the first current source/sink circuit for sourcing first and second current magnitudes, the first current magnitude being different from the second current magnitude, and the controller provides at least one control signal to the first voltage measurement circuit for measuring first and second voltages associated with the first defibrillation electrode and the respective first and second current magnitudes.

16. The apparatus of claim 15, wherein the controller provides at least one control signal to the second current source/sink circuit for sourcing third and fourth current magnitudes, the third current magnitude being different from the fourth current magnitude.

17. The apparatus of claim 16, further comprising a second voltage measurement circuit coupled to the second defibrillation electrode, wherein the controller provides at least one control signal to the second voltage measurement circuit for measuring third and fourth voltages associated with the second defibrillation electrode and the respective third and fourth current magnitudes.

18. The apparatus of claim 15, wherein the controller includes a lead impedance measurement module that calculates a lead impedance based on a quotient of the difference between the first and second voltage measurements and a difference between the first and second current levels.

19. The apparatus of claim 18, including a calibration module that adjusts the lead impedance based on measured values of a plurality of resistances and associated known resistance values.

20. An apparatus for determining an impedance between first and second defibrillation electrodes, the apparatus comprising:

a first current source/sink circuit;

a first diode, coupling the first current source/sink circuit to the first defibrillation electrode;

a first voltage measurement circuit, coupled to the first defibrillation electrode through the first diode;

a second current source/sink circuit;

a second diode, coupling the second current source/sink circuit to the second defibrillation electrode; and a second voltage measurement circuit, coupled to the second defibrillation electrode through the second diode.

21. The apparatus of claim 20, in which the first and second current source/sink circuits are the same circuit.

22. The apparatus of claim 20, in which the first and second voltage measurement circuits are the same circuit.

23. The apparatus of claim 20, further comprising a controller, providing control signals to the first and second current source/sink circuits for sourcing a first charge at the first electrode and sinking a second charge at the first electrode, wherein the first and second charges are approximately equal in magnitude.

24. An apparatus for determining an impedance between first and second defibrillation electrodes, the apparatus comprising:

a first diode, coupled to the first defibrillation electrode;

a second diode, coupled to the second defibrillation electrode;

a first current source/sink circuit;

a first voltage measurement circuit; and a multiplexer circuit, coupling at least one of the first current source/sink circuit and the first voltage measurement circuit to each of the first and second defibrillation electrodes through the respective first and second diodes.

25. An apparatus comprising:

first and second defibrillation electrodes;

a first diode having an anode and a cathode, the cathode of the first diode coupled to the first defibrillation electrode;

a second diode having an anode and a cathode, the cathode of the second diode coupled to the second defibrillation electrode;

a first current source/sink circuit, coupled to the anode of the first diode;

a second current source/sink circuit, coupled to the anode of the second diode;

a controller, providing control signals to the first and second current source/sink circuits for sourcing a first charge at the first electrode and sinking a second charge at the first electrode, wherein the first and second charges are approximately equal in magnitude;

a first differential voltage measurement circuit, coupled to the anode of the first diode;

a first switching device, coupling the first defibrillation electrode to a ground node;

a second switching device, coupling the second defibrillation electrode to the ground node; and a defibrillation output supply, coupled to the first defibrillation electrode through a third switching device, and coupled to the second defibrillation electrode through a fourth switching device.

26. The apparatus of claim 25, further comprising:

a first zener diode, including an anode coupled to the ground node and a cathode coupled to the anode of the first diode; and a second zener diode, including an anode coupled to the ground node and a cathode coupled to the anode of the second diode.

27. The apparatus of claim 25, further comprising:

a multiplexer, coupling the first differential voltage measurement device to the anodes of each of the first and second diodes.

28. The apparatus of claim 25, in which the first and second current source/sink circuits are the same circuit, and further comprising a multiplexer coupling the first and second current source/sink circuits to the anodes of each of the first and second diodes.

* * * * *